United States Patent
Sepper et al.

(10) Patent No.: US 12,161,661 B2
(45) Date of Patent: Dec. 10, 2024

(54) TOPICAL COMPOSITION FOR DESTROYING, IN VIVO, AN EXTERNAL HYPERPLASTIC TISSUE, SUCH AS, BUT NOT LIMITED TO, A VIRAL SKIN LESION, SUCH AS, BUT NOT LIMITED TO, A VIRAL WART

(71) Applicants: Alexander Sepper, New York, NY (US); Dennis Tubian, New York, NY (US); John Navi, New York, NY (US)

(72) Inventors: Alexander Sepper, New York, NY (US); Dennis Tubian, New York, NY (US); John Navi, New York, NY (US)

(*) Notice: Subject to any disclaimer, the term of this patent is extended or adjusted under 35 U.S.C. 154(b) by 125 days.

(21) Appl. No.: 18/112,852

(22) Filed: Feb. 22, 2023

(65) Prior Publication Data
US 2024/0024351 A1 Jan. 25, 2024

Related U.S. Application Data

(63) Continuation-in-part of application No. 17/872,816, filed on Jul. 25, 2022.

(51) Int. Cl.
| | |
|---|---|
| *A61P 17/02* | (2006.01) |
| *A61K 9/00* | (2006.01) |
| *A61K 31/19* | (2006.01) |
| *A61K 31/4172* | (2006.01) |
| *A61K 31/724* | (2006.01) |
| *A61K 33/34* | (2006.01) |
| *A61K 33/44* | (2006.01) |

(52) U.S. Cl.
CPC .......... *A61K 31/724* (2013.01); *A61K 9/0014* (2013.01); *A61K 31/19* (2013.01); *A61K 31/4172* (2013.01); *A61K 33/34* (2013.01); *A61K 33/44* (2013.01); *A61P 17/02* (2018.01)

(58) Field of Classification Search
CPC ... A61P 17/02; A61K 9/0014; A61K 2800/10; A61K 45/06
See application file for complete search history.

(56) References Cited

U.S. PATENT DOCUMENTS

| | | | | |
|---|---|---|---|---|
| 4,595,591 | A * | 6/1986 | Mardi | A61K 33/38 424/718 |
| 5,928,631 | A * | 7/1999 | Lucas | A61K 8/27 424/405 |
| 5,942,501 | A * | 8/1999 | Hayward | B82Y 5/00 514/58 |
| 2010/0003325 | A1* | 1/2010 | Herman | A61K 45/06 514/159 |
| 2020/0360247 | A1* | 11/2020 | Giniger | A61K 8/062 |

FOREIGN PATENT DOCUMENTS

| | | | | |
|---|---|---|---|---|
| CA | 2766630 A1 * | 11/2012 | | A61K 31/706 |
| EP | 0413528 A1 * | 2/1991 | | |
| WO | WO-03047604 A1 * | 6/2003 | | A61K 31/19 |
| WO | WO-2015159206 A1 * | 10/2015 | | A61K 33/34 |

* cited by examiner

*Primary Examiner* — Tracy Liu

(57) ABSTRACT

A topical composition that destroys an external hyperplastic tissue, while preserving a basic architecture of the external hyperplastic tissue rather than dissolution of hydrolysis of protein peptide bonds of the external hyperplastic tissue, thereby providing a timely regeneration of healthy skin tissue after the external hyperplastic tissue has been treated with the topical composition, and thereby contributing to less damage to surrounding healthy skin tissue, as a result of, destructive potential of the topical composition being effectively neutralized and penetration of the topical composition into the surrounding healthy tissue being effectively blocked. The topical composition includes a caustic portion and a detoxifying and cleansing portion. The caustic portion has a caustic effect on the external hyperplastic tissue. The detoxifying and cleansing portion is a white activated charcoal powder, has a detoxifying and cleansing effect on the external hyperplastic tissue, and has silicon dioxide as an active substance.

27 Claims, 18 Drawing Sheets

| CAUSTIC PORTION 32 | |
|---|---|
| INGREDIENTS | CONCENTRATIONS GIVEN IN WT/VOL% |
| First distilled water (38) | 1.5-31.4 - optimally 23.00 |
| B-Cyclodextrin (HPBC) (40) | optimally 2.00 |
| Copper (II)-nitrate trihydrate (42) | 0.001-0.2 - optimally 0.004 |
| Cadmium nitrate tetrahydrate (44) | 0.23-1.3 - optimally 0.432 |
| Oxalic acid dihydrate (46) | 3.2-6.78 - optimally 5.45-5.925 |
| 90% Lactic acid (48) | 0.6-3.87 - optimally 1.325 |
| Pyruvic acid (50) | .022-1.94 - optimally 0.042 |
| Acetic acid (52) | 1.05-7.22 - optimally 4.00-4.005 |
| 65% Nitric acid (54) | 14.6-72.45 - optimally 50.4-50.7 |
| Metallic copper powder (56) | optimally 0.10 |
| Maleic acid (58) | optimally 0.10 |
| L-Histidine (60) | optimally 0.15 |
| Second distilled water (62) | 8.6-44.3 - optimally 36.00 |

FIG. 3

| ASSESSMENT OF THE WART | |
|---|---|
| Amount and location of skin warts | 1 at Frown Area |
| Size of each wart | 5 x 5 |
| Color of the wart and color change after procedure | Skin Color |
| Integrity of the wart (cracks, scratches, calluses etc.) | None |
| Existence of inflammation (redness) | None |
| Existence of hemorrhages | None |
| Existence of pigmentation | None |
| Pain or excessive sensitivity of the wart | None |
| ASSESSMENT OF THE SURROUNDING SKIN | |
| Integrity of the surrounding skin (cracks, scratches, calluses etc.) | None |
| Existence of inflammation (redness) | None |
| Existence of hemorrhages | None |
| Existence of pigmentation | None |

FIG. 5A

In 3 minutes

| ASSESSMENT OF THE WART | |
|---|---|
| Amount and location of skin warts | 1 at Frown Area |
| Size of each wart | 5 x 5 |
| Color of the wart and color change after procedure | White |
| Integrity of the wart (cracks, scratches, calluses etc.) | None |
| Existence of inflammation (redness) | None |
| Existence of hemorrhages | None |
| Existence of pigmentation | None |
| Pain or excessive sensitivity of the wart | None |
| ASSESSMENT OF THE SURROUNDING SKIN | |
| Integrity of the surrounding skin (cracks, scratches, calluses etc.) | None |
| Existence of inflammation (redness) | Perifocal |
| Existence of hemorrhages | None |
| Existence of pigmentation | None |

FIG. 5B

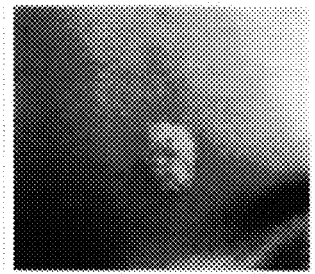

In 6 minutes

| ASSESSMENT OF THE WART | |
|---|---|
| Amount and location of skin warts | 1 at Frown Area |
| Size of each wart | 5 x 5 |
| Color of the wart and color change after procedure | White-Gray |
| Integrity of the wart (cracks, scratches, calluses etc.) | None |
| Existence of inflammation (redness) | None |
| Existence of hemorrhages | None |
| Existence of pigmentation | None |
| Pain or excessive sensitivity of the wart | None |
| ASSESSMENT OF THE SURROUNDING SKIN | |
| Integrity of the surrounding skin (cracks, scratches, calluses etc.) | None |
| Existence of inflammation (redness) | Perifocal |
| Existence of hemorrhages | None |
| Existence of pigmentation | None |

FIG. 5C

| In 15 minutes | ASSESSMENT OF THE WART | |
|---|---|---|
| | Amount and location of skin warts | 1 at Frown Area |
| | Size of each wart | 5 x 5 |
| | Color of the wart and color change after procedure | Gray |
| | Integrity of the wart (cracks, scratches, calluses etc.) | None |
| | Existence of inflammation (redness) | None |
| | Existence of hemorrhages | None |
| | Existence of pigmentation | None |
| | Pain or excessive sensitivity of the wart | None |
| | ASSESSMENT OF THE SURROUNDING SKIN | |
| | Integrity of the surrounding skin (cracks, scratches, calluses etc.) | None |
| | Existence of inflammation (redness) | Perifocal |
| | Existence of hemorrhages | None |
| | Existence of pigmentation | None |

FIG. 5D

| In 15 minutes | ASSESSMENT OF THE WART | |
|---|---|---|
| | Amount and location of skin warts | 1 at Frown Area |
| | Size of each wart | 5 x 5 |
| | Color of the wart and color change after procedure | Gray |
| | Integrity of the wart (cracks, scratches, calluses etc.) | None |
| | Existence of inflammation (redness) | None |
| | Existence of hemorrhages | None |
| | Existence of pigmentation | None |
| | Pain or excessive sensitivity of the wart | None |
| | ASSESSMENT OF THE SURROUNDING SKIN | |
| | Integrity of the surrounding skin (cracks, scratches, calluses etc.) | None |
| | Existence of inflammation (redness) | Perifocal |
| | Existence of hemorrhages | None |
| | Existence of pigmentation | None |

FIG. 5E

| In 8 hours | ASSESSMENT OF THE WART | |
|---|---|---|
| | Amount and location of skin warts | 1 at Frown Area |
| | Size of each wart | 5 x 5 |
| | Color of the wart and color change after procedure | Brown |
| | Integrity of the wart (cracks, scratches, calluses etc.) | None |
| | Existence of inflammation (redness) | None |
| | Existence of hemorrhages | None |
| | Existence of pigmentation | None |
| | Pain or excessive sensitivity of the wart | None |
| | ASSESSMENT OF THE SURROUNDING SKIN | |
| | Integrity of the surrounding skin (cracks, scratches, calluses etc.) | None |
| | Existence of inflammation (redness) | Perifocal |
| | Existence of hemorrhages | None |
| | Existence of pigmentation | None |

FIG. 5F 37 year-old male with two warts at forehead area of head.
Sizes of warts: 5 and 6 mm.
The topical composition (20) was applied once by means of capillary applicator.
At the end of day 3 both warts became mummified.
On day 8 the surface of patient's skin was completely cleared from existed warts.

29 year-old female with a wart at chin area.
Size of wart: 10 mm.

The topical composition (20) was applied by alternating two cycles with 5 min intervals.
In 5 min the wart became whitish-gray.
At day 3 the wart became mummified.
At day 6 the wart was almost ready to shed.
On day 9 the mummified ward shed out.

At 3 weeks the surface of the patient's skin was completely cleared from existing wart.

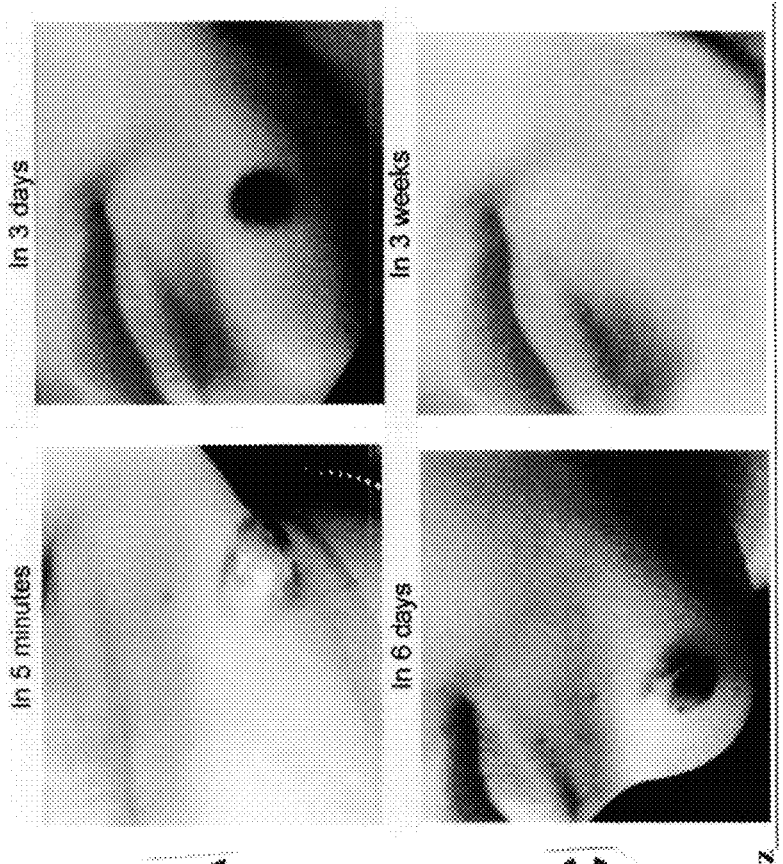

FIG. 7A
FIG. 7B
FIG. 7C
FIG. 7D 46 year-old female with keratinized wart on the phalanx of the fourth finger.
Size of wart: 12 mm.
The composition (20) was applied by alternating 4 cycles with 5 min intervals.
In 15 min the wart became whitish-gray.
At day 5 the wart became mummified.
On day 10 the wart was almost ready to shed.
On day 14 the mummified wart shed out.
After 2 months the patient's skin was cleared of existing war 16 year-old male with 6 warts at the base of the thumb.
Sizes of warts: 5 mm (2) and 2 mm (4).
The topical composition (20) was applied to warts
3 cycles with 5 min intervals during 15 days.
All four 2 mm warts resolved and 5 mm warts decreased twice in size.

54 year-old male with plantar warts at the heel area.
Sizes of warts: from 3 to 10 mm.
The topical composition (20) was applied by alternating 5 cycles with 5 min intervals.
After one month the patient's skin was cleared of warts.

58 year-old male with 3 pigmented warts at the left side of face.
Sizes of warts: 6 mm (1) and 2 mm (2).
The topical composition (20) was applied to warts during 15 days.
As a result of the treatment all warts decreased twice in size.

| Area of Wart Location | Size of the Wart | | | | | Total |
|---|---|---|---|---|---|---|
| | less than 1.0 mm | more than 1.0-2.0 mm | more than 2.0-3.0 mm | more than 3.0-4.0 mm | more than 4.0-5.0 mm | |
| Hands | 21 | 34 | 11 | 5 | 2 | 73 |
| Feet | 7 | 17 | 10 | 3 | 1 | 38 |
| Face | 10 | 16 | 11 | 5 | 4 | 46 |
| Neck | 12 | 12 | 8 | 1 | 0 | 33 |
| Body | 14 | 20 | 14 | 4 | 2 | 54 |
| Total | 64 | 99 | 54 | 18 | 9 | 244 |

FIG. 12

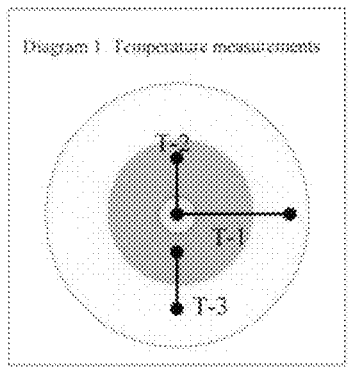

FIG. 13

| Table 3. Criteria of Temperature Analysis |
|---|
| T-1 - temperature difference between area of the wart and intact skin |
| T-2 - temeparature difference between area of the wart and area of skin redness |
| T-3 - temeparature difference between area of skin redness and intact skin |

FIG. 14

A 32-year-old male with three warts at the area of the right forearm. Sizes of the three warts included one wart up to 1.0 mm, and two warts up to 2.0 mm. The topical composition (20) was applied three times a day for 2 weeks. At the end of day 10, the sizes of warts decreased up to 60-65%. At the end of day 15, the surface of patient's skin was completely cleared from existed warts.

Initially

In day 15

TOPICAL COMPOSITION FOR DESTROYING, IN VIVO, AN EXTERNAL HYPERPLASTIC TISSUE, SUCH AS, BUT NOT LIMITED TO, A VIRAL SKIN LESION, SUCH AS, BUT NOT LIMITED TO, A VIRAL WART

CROSS REFERENCE TO RELATED APPLICATIONS

The instant non-provisional patent application is a Continuation-In-Part non-provisional patent application of non-provisional patent application Ser. No. 17/872,816, filed on 25 Jul. 2022, in group art unit 1617, entitled TOPICAL ANTIVIRAL LIQUID FOR TREATMENT OF WARTS, and which claims priority from provisional patent application Nos. 63/227,151 filed 29 Jul. 2021, and 63/227,144 filed 29 Jul. 2021 and 63/227,147 filed 29 Jul. 2021, and entitled TOPICAL ANTIVIRAL LIQUID FOR AFFECTING ETIOLOGICAL FACTORS OF VIRAL WARTS, and are all incorporated herein in their entireties by reference thereto.

BACKGROUND OF THE INVENTION

Field of the Invention

The embodiments of the present invention relate to a topical composition, more particularly, the embodiments of the present invention relate to a topical composition for destroying, in vivo, an external hyperplastic tissue, such as, but not limited to, a viral skin lesion, such as, but not limited to, a viral wart, while preserving a basic architecture of the external hyperplastic tissue rather than dissolution of hydrolysis of protein peptide bonds of the external hyperplastic tissue, thereby providing a timely regeneration of healthy skin tissue after the external hyperplastic tissue has been treated with the topical composition, and thereby contributing to less damage to surrounding healthy skin tissue, as a result of, destructive potential of the topical composition being effectively neutralized and penetration of the topical composition into the surrounding healthy tissue being effectively blocked.

Description of the Prior Art

The treatment of various skin tumors, namely, electro-cauterization, cryo-surgery, as well as, radiotherapy and chemotherapy or plastic surgery, are not always fully satisfactory, Malignant tumors or those suspected of being malignant are excised deeply out of the healthy tissue, mostly after sample excision. This procedure and sometimes necessary plastic surgical measures are particularly difficult near the eyes or in the nose region or not possible at all in the case of multiple lesions and recurrences, e.g., in an area previously treated by radiotherapy. The method of Mobs which after prior treatment with trichloroacetic acid and zinc chloride allows the successive removal of the pathological tissue and subsequent histological control, but is not satisfactory, as a result of, the considerable painfulness.

After acne, warts are the most common dermatological complaint. Three out of four people will develop a wart, verruca vulgaris, at some time in their lives. Warts are slightly contagious, and can spread to other parts of the body by touching them or shaving around infected areas. Children and young adults are more prone to getting warts, as a result of, their defense mechanisms may not be fully developed. It is possible, however, to get a wart at any age.

Warts are caused by the human papilloma virus (HPV), which enters the skin through a cut or scratch and causes cells to multiply rapidly. Usually, warts spread through direct contact. Each person responds differently, and not everyone exposed to HPV will develop a wart.

Patients with warts seek advice from cosmetologists, general practitioners, pharmacists, naturopaths, allied health professionals, family or friends, dermatologists, and others. Unfortunately, even with years of medical literature on this subject, high-quality level 1 evidence for the efficacy of almost all previous treatments is nonexistent.[1] No treatment has yet proven 100% effective for a cure. Pain related to treatment, side effects, and costs could be determining factors in choosing a therapy.[2]

[1]Gibbs, S and others; BMJ2002; 325:461 and Sterling, J C and others; BEJDermatol 2001; 144:4-11.

[2]Stolberg, D L and others; Am. Fam. Physician 2003; 67:1233-1240.

Treatments for destroying various skin tumors have been provided in the prior art, which are incorporated herein in their entirety by reference thereto. Even though these treatments may be suitable for the specific individual purposes to which they address, nevertheless, they differ from the embodiments of the present invention in that they do not teach a topical composition for destroying, in vivo, an external hyperplastic tissue, such as, but not limited to, a viral skin lesion, such as, but not limited to, a viral wart, while preserving a basic architecture of the external hyperplastic tissue rather than dissolution of hydrolysis of protein peptide bonds of the external hyperplastic tissue, thereby providing a timely regeneration of healthy skin tissue after the external hyperplastic tissue has been treated with the topical composition, and thereby contributing to less damage to surrounding healthy skin tissue, as a result of, destructive potential of the topical composition being effectively neutralized and penetration of the topical composition into the surrounding healthy skin tissue being effectively blocked. Some examples are stated below.

Caustic Agents in General

For centuries, caustic agents, in particular strong acids, have been used to "burn out" cutaneous lesions, warts, and the like. Not all strong acids, however, are equally popular, as a result of, the quite varying nature of their effects on integumental proteins. The treatments with caustic agents, however, often leave more or less ugly scars.[3]

[3]R. Volk and F. Winter, Lexicon der kosmetischen Praxis, Julius Springer Editor, Vienna 1936, page 677; K. O. Moller, Pharmacology, 2nd German edition, Benno Schwabe & Co., Basle 1953, pages 167 and 584.

The therapeutical use of caustic agents for treating skin cancer is expressly declined[4] as a result of, too great a risk of not completely removing the carcinoma, and afterwards, it is often noticed that an insufficiently treated carcinoma suddenly begins to again proliferate rapidly.

[4]R. Volk and F. Winter, loc. cit., page 308.

Nitric Acid, Salicylic Acid, Some Halogenated Acetic Acids, and Hydrochloric Acid Concentrated solutions of nitric acid, salicylic acid, and some halogenated acetic acids have gained more or less specific niches in the armamentarium of dermatologists, while hydrochloric acid, for example, is rarely used.[5]

[5]H. W. Felter, The Eclectic Materia Medica Pharmacology and Therapeutics, John K. Scudder Publisher, Cincinnati (OH, USA), 1922, page 133; A. L. Welsh, The Dermatologist's Handbook, C. C. Thomas Publisher, Springfield (USA) 1957, page 111; C. J. Lunsford et al, Arch. Dermot. and Syph. 68 (1953), 148.

Lactic Acid and Oxalic Acid

Still with the purpose of burning out warts, lactic acid and oxalic acid have been proposed too.[6] The keratolytic effect of these acids, however, is small and they are therefore almost always used in combination with salicylic acid.[7] For example, a composition is sold in the USA under the name of COMPOUND W WART REMOVER®, which contains acetic acid and salicylic acid.[8]

[6]H. W. Felter, loc. cit.), as well as, acetic acid (F. P. Foster, Practical Therapeutics, D. Appleton and Co., 1897, page 226.
[7]German Publ. Patent Appl'n No. 1,266,448.
[8]Handbook of Nonprescription Drugs, 5th edition, American Pharmaceutical Association 1977, pages 364 and 368.

Composition of Glycolic Acid, Citric Acid, Malic Acid, Tartronic Acid, Tartaric Acid, Glucuronic Acid, Pyruvic Acid, Methyl Pyruvate, Ethyl Pyruvate, and 2-Hydroxyisobutyric Acid or 3-Hydroxybutyric Acid A composition including glycolic acid, citric acid, malic acid, tartronic acid, tartric acid, glucuronic acid, pyruvic acid, methyl pyruvate, ethyl pyruvate, and 2-hydroxyisobutyric acid or 3-hydroxybutyric acid alleviates the symptoms of hyper-keratinization conditions, e.g., acne and palmar or plantar hyperkeratosis.

Metallic Salts

In the 19th century, various metallic salts have been proposed for removing warts and other skin defects. Among others are copper salts like the acetate and the sulfate of lead salts in combination with zinc sulfate, copper sulfate, and white vinegar.

Furthermore, others include antimony, arsenic, chromium, mercury, and silver salts,[9] as well as, cadmium salts.[10] Among all these salts, only zinc chloride, when used together with trichloroacetic acid in the Mohs method, have reached some short-lived importance for treating skin cancer.

[9]C. J. Lunsford, loc. cit.
[10]S. O. L. Potter, Therapeutic Materia Medica and Pharmacy, P. Blakiston's Son and Co., Philadelphia (PA, USA) 1909 page 185.

Mixture of Copper Nitrate and Lactic Acid

An agent for treating benign tumors and precancerous diseases of the skin includes a mixture of copper nitrate and lactic acid. The mixture is carried out by mixing copper nitrate containing nitric acid and lactic acid in the proportions of 1:2 and 3:1, respectively. Experimental follow-up work with this agent, however, has evidenced an instability that can cause bursting of the bottle it is stored in.

Salicylic Acid 15-26% salicylic acid treatment is used locally every day for 3 to 4 months after removal of hyperkeratosis. Qualitative studies have shown that the effect of the salicylic acid is low and patients find the treatment uncomfortable, as a result of, irritation of the surrounding skin. The average cure rate was 49%, with a range of 0-69%. Very low concentration of salicylic acid can cause chemical burns and should not be used in areas with poor regeneration.

Cryotherapy

Cryotherapy involves 15-30 sec. exposition of freezing with repeated procedures every 2-4 weeks for 3 months. The effectiveness of cryotherapy treatment of warts at various parts of the body is in the range from 0% to 69%, with a mean of 49%.

Furthermore, cryotherapy is most effective for hand warts and the least effective for plantar warts. Patients should be advised that cryotherapy is a painful therapy. Side effects are usually observed in the reduction of the recommended interval between treatments. Care should be taken when using cryotherapy close to cutaneous nerves, tendons, and nails, as well as, in patients with impaired arterial or venous circulation. Hypo or hyper-pigmentation particularly in patients with darker skin types can be a side effect of the therapy.

Bleomycin 0.1-1 mg of bleomycin is injected into the wart after local anesthesia. Very painful during and after treatment. Compared with cryotherapy, bleomycin shows better results, with cure rate in 92-97% vs. 76-82%. The main side effect of bleomycin is the pain during injection and for up to 48 hours after it. Post-inflammatory hyperpigmentation is possible, which usually goes away after a few weeks.

Contact Immunotherapy

Diphenylcyclopropenone DPC or squaric acid dibutylester SADBE contact immunotherapy is given twice a week every 3 weeks for 3-6 months. Year retrospective review of 48 patients with warts on the palms and soles treated with DPC showed complete disappearance of warts in 88%. The average processing time was 5 months and no recurrence was observed within 2 years. Although efficacy of this therapy in immunocompromised patients is reduced, this therapy can be effective.

Ftoruracil

5% Ftoruracil cream (5-FU) is given every day for 4-12 weeks. In one study, 5% cream 5-FU was applied to warts of the hands and legs once a day for 4 weeks, with occlusion on one side of the body, while simultaneously, a placebo cream was applied to the warts on the other side of the body. At the end of treatment, 60% of the warts were cleared on the side treated with the 5-FU compared to 17% for the placebo side. In another study, treatment of plantar warts in adults for 12 weeks resulted in a complete cure in 95% of patients (19/20) and 10% in the placebo group.

Laser Therapy

Laser therapy involves from 2 to 4 procedures in a dosage of 7:10 J per $cm^2$. $CO_2$ laser, neodymium yttrium aluminum garnet (Nd:YAG), Er:YAG, an infrared laser phosphate, and potassium titanyl were also used in a small amount of cohort studies. Best results were achieved in 96% of 369 patients using the Nd:YAG laser.

Acupuncture

Auricular acupuncture is given once a week for 10 weeks. The effect of acupuncture is achieved in 53% (16/30) of the patients compared with 3% (1 of 30) in a group of tretinoin.

Cantharidin

A 0.7% cantharidin solution is given every 3 weeks (4 procedures). A study of 15 patients who were treated with 0.7% sodium cantharidin over flat warts on the face showed a cure in all 15 patients over 16 weeks on average for 359 procedures.

Cidofovir

A 1% cidofovir cream is used every day for 5 days per week for 8 weeks. Cidofovir has been used intrafocally an average of 3.2 injections per course, with a resolution of 98% of warts in the open label study. Side effects include nephrotoxicity, neutropenia, and metabolic acidosis.

Formaldehyde

A 3-4% formaldehyde solution is applied for 15-20 min. every day for 8 weeks. Formaldehyde was effective in 80% of 646 children treated. This study used 3% formaldehyde. The concentration can be increased. Formaldehyde also is available as a 0.75% gel. Formaldehyde, however, can cause allergies.

Glutaraldehyde

A 10% glutaraldehyde solution is applied every day for 3 months. Glutaraldehyde solution at 10% efficiency with plantar warts equivalent to the solution of salicylic acid. In 25 patients with resistant warts, an effectiveness of 72% was shown. Treatment was well tolerated in children. Glutaraldehyde should be used with caution, especially in concentrations of 10%, as a result of, reports of deep necrosis with repeated use.

Hyperthermia

Hyperthermia involves warming of warts to 40-44° C. for 30 min. for 4-5 days. Cure was achieved in 54% (15/28) versus 12% (3 of 26) in the placebo group. Another study involving 13 patients with warts on the hands also suggested that localized hyperthermia can be quite effective and a safe method.

Imiquimod

A 5% Imiquimod cream is applied twice a day for 6 months. Two open studies showed a 50% egression of warts in 76% of patients treated twice daily for up to 24 weeks and 9.5 weeks after the curing treatment in 56% of the 50 patients of whom 19 had immunosuppression.

Phenol

An 80% Phenol solution is used every week for 6 weeks. The cure rate of patients with cryotherapy was 70% and 83% when using phenol, although termination of treatment in the group of phenol was frequent.

Photodynamic Therapy

ALA-PDT photodynamic therapy involves up to 3 procedures. Studies have been reported on the effectiveness of PDT with warts in 58%-95% cases. PDT may be used in combination with a laser. In that study, 12 patients with periungual warts treated with $CO_2$ followed by fractional laser reception methyl5-aminolaevuninic acid (MAL) 5PDT. 3 hours, 50 J cm 52, 15 minutes, once in two weeks of treatment for 6 weeks achieved a cure rate of 90%.

In another study, 19 patients with warts on the hands and feet were treated with MAL-PDT plus light source PDL providing a resolution of 53% of treated warts. The warts on the hands cleaned more effectively than the plantar warts.

Podophyllin

A 25% podophyllin in liquid paraffin is used. In a very small open label study of 40 patients with plantar warts treated with 25% podophyllin in liquid paraffin for prolonged occlusion plaster, with about 67% of patients were treated within 3 months. The side effects of the treatment, however, include an intense very painful inflammatory reaction.

Pyruvic Acid

A 70% Pyruvic acid solution is used every day for 2 months. Use of pyruvic acid leads to recovery of 70% of patients, and in combination with 0.5% 5-FU 5, 80% of patients. Addition of 5-FU does not practically increase effect. Hypertrophic scars have been reported in patients with warts on the hands and chest using 98% pyruvic acid in combination with 2% of 5-FU.

Etretinate

In an observational study where children aged 2.5-12.5 years old were treated with oral etretinate, and within 3 months the effect was observed in 80% (16/20). Open study of children and adult patients with flat warts on the face showed effect in 73% after 2 months of treatment with isotretinoin in dose of 0.5 mg/kg. per day.

Surgical Treatment (Curettage)

There are no high-quality studies on the effectiveness of surgical treatment—such as, curettage cauterization and $CO^2$ laser, although these treatments are widely used. In 50 patients with solitary plantar warts treated with electric wave therapy radio waves with a frequency of 2.4 MHz, achieved a cure in 67% of the patients.

Trichloroacetic Acid

A 50-80% trichloroacetic acid solution is used every day for 8 weeks. Monochloroacetic acid with formaldehyde had no effect on the efficiency. Monochloroacetic acid is a highly toxic substance that can form skin erosion.

Vitamin D Analogs

Vitamin D analogs, such as, macsacalcitole, is used 3 times a day for 2-6 months or calcipotriol is used once a day for 2-3 months.

Other

A topically applied composition has been found, which superficial lesions of the skin and of the mucous membranes of benign, premalignant, and malignant type can be successfully treated. Among these lesions and tumors of the skin and of the mucous membranes, which are detrimental to the bodily beauty, but which in the vernacular do not constitute illnesses, e.g., warts, birthmarks, naevus, hemangioma, and callus, as a result of age, but also benign skin diseases and finally precancerous conditions and malignant tumors.

U.S. Pat. No. 3,920,835 to Van Scott et al

U.S. Pat. No. 3,920,835—issued to Van Scott et al. on 18 Nov. 1975 in US class 424 and subclass 311—teaches a treatment to alleviate the symptoms of diseases characterized by defects in keratinization. The treatment includes a topical application of an ointment or lotion containing one or more lower aliphatic compounds having from two to about six carbon atoms, and preferably, having Alpha-carbon functionality. The ointment includes Alpha-hydroxy acids, keto acids and esters thereof, and 3-hydroxybutyric acid. and is includable with one or more of the compounds present in a total of from 1 to 20% in either a water or a alcohol solution or an ointment.

U.S. Pat. No. 3,988,470 to Van Scott et al.

U.S. Pat. No. 3,988,470 issued to Van Scott et al. on 26 Oct. 1976 in class 424 and subclass 283, teaches a treatment to alleviate the symptoms of diseases characterized by defects in keratinization. The treatment includes the topical application of an ointment or lotion containing one or more lower aliphatic compounds having from 2 to about 6 carbon atoms, and preferably. having α-carbon functionality. The ointment includes α-hydroxy acids, keto acids and esters thereof, and 3-hydroxybutyric acid, and is includable with one or more of the compounds present in a total amount of from 1 to 20% in either a water or alcohol solution or an ointment.

U.S. Pat. No. 4,595,591A to Mardi et al.

U.S. Pat. No. 4,595,591A issued to Mardi et al. on 17 Jun. 1986 in U.S. class 424 and subclass 127, teaches a composition consisting of an aqueous solution of nitric acid and nitrous acid, with a pH value below 1, an acid equivalent of from 6 to 10 mmol/ml, and with an amount of nitrous acid corresponding to 0.01 to 5 mg. of nitrite ($NO_2$) per ml. Additionally, the aqueous solution, preferably, contains acetic acid, oxalic acid, and lactic acid, as well as, copper and cadmium ions. A method of making includes mixing the components and letting them react to the end or by an oxidative method, in the course of which nitrous acid is formed.

In contradiction, however, the topical composition of the embodiments of the present invention teaches, and explicitly discloses, the additional ingredients of white activated charcoal powder, b-cyclodextrine (HPBC), 1-histidine, and metallic copper powder, which are not explicitly, or even implicitly, disclosed by Mardi et al.

The composition of Mardi et al. explicitly discloses 3.12 wt/vol % of cadmium nitrate tetrahydrate and is silent as to explicitly, or even implicitly, disclosing the white activated charcoal powder of the embodiments of the present invention. In contradistinction, however, the topical composition of the embodiments of the present invention teaches, and explicitly discloses, cadmium nitrate tetrahydrate in a range of 0.23-0.1.3 wt/vol % optimally 0.432—which has been substantiated by extensive experimental work.

In further contradiction, however, the topical composition of the embodiments of the present invention teaches, and explicitly discloses, timely regeneration of healthy skin tissue after the external hyperplastic tissue has been treated with the topical composition, which is not explicitly, or even implicitly, disclosed by Mardi et al.

In still further contradiction, however, the topical composition of the embodiments of the present invention teaches, and explicitly discloses, the elimination of hydrolysis of protein peptide bonds of the external hyperplastic tissue that was treated with the topical composition, which is not or even implicitly, disclosed by Mardi et al.

In yet further contradiction, however, the topical composition of the embodiments of the present invention teaches, and explicitly discloses, a destruction potential that is effectively neutralized, which is not explicitly, or even implicitly, disclosed by Mardi et al.

In still yet further contradiction, however, the topical composition of the embodiments of the present invention teaches, and explicitly discloses, the elimination of undesirable maceration, inflammatory, or coarse keratolytic process that can lead to the spread of the virus to other skin areas, which is not explicitly, or even implicitly, disclosed by Mardi et al.

Thus, as shown, supra, Mardi et al. is silent as to explicitly, or even implicitly, disclosing the following results, which are taught, and explicitly disclosed, by the topical composition of the embodiments of the present invention[11]:

[11] *Ex parte Tanaka, Marushima and Takahashi,* 174 USPQ 38 ("Claims are not rejected . . . if the prior art devices do not accomplish applicant's result." [Emphasis added]. in In re Dillon, 919 F.2d 688, 692 (Fed. Cir. 1990) ("A prima facie case of . . . [unpatentability] requires that the prior art suggest the . . . problem the applicant attempts to solve." [Emphasis added].

Cadmium nitrate tetrahydrate in a range of 0.23-0.1.3 wt/vol %;

Timely regeneration of healthy skin tissue after the external hyperplastic tissue has been treated with the topical composition of the embodiments of the present invention, which is accomplished by the white activated charcoal powder and the 1-histidine. and which is not explicitly disclosed by Mardi et al.;

Elimination of hydrolysis of protein peptide bonds of the external hyperplastic tissue;

Destruction potential that is effectively neutralized; and

Elimination of undesirable maceration, inflammatory, or coarse keratolytic process that can lead to the spread of the virus to other skin areas.

It is apparent, supra, that numerous approaches have been provided in the prior art, which are adapted to be used. Furthermore, even though these approaches may be suitable for the specific individual purposes to which they address, nevertheless, they would not be suitable for the purposes of the embodiments of the present invention, as heretofore described. Namely, prior to the topical composition of the embodiments of the present invention, there was nothing that can destroy or remove the causative factor responsible for skin viral warts, papillomavirus, from the body. Therefore, the treatment of human papilloma virus was limited to the local removal of warts or immune corrective course of therapy.

Thus, there exists a need for atopical composition for destroying, in vivo, an external hyperplastic tissue, such as, but not limited to, a viral skin lesion, such as, but not limited to, a viral wart, while preserving a basic architecture of the external hyperplastic tissue rather than dissolution of hydrolysis of protein peptide bonds of the external hyperplastic tissue, thereby providing a timely regeneration of healthy skin tissue after the external hyperplastic tissue has been treated with the topical composition, and thereby contributing to less damage to surrounding healthy skin tissue, as a result of, destructive potential of the topical composition being effectively neutralized and penetration of the topical composition into the surrounding healthy tissue being effectively blocked.

SUMMARY OF THE INVENTION

Thus, an object of the embodiments of the present invention is to provide a topical composition for destroying, in vivo, an external hyperplastic tissue, such as, but not limited to, a viral skin lesion, such as, but not limited to, a viral wart, while preserving a basic architecture of the external hyperplastic tissue rather than dissolution of hydrolysis of protein peptide bonds of the external hyperplastic tissue, thereby providing a timely regeneration of healthy skin tissue after the external hyperplastic tissue has been treated with the topical composition, and thereby contributing to less damage to surrounding healthy skin tissue, as a result of, destructive potential of the topical composition being effectively neutralized and penetration of the topical composition into the surrounding healthy tissue being effectively blocked; which avoids the disadvantages of the prior art.

Briefly stated, another object of the embodiments of the present invention is to provide a topical composition that destroys, in vivo, external hyperplastic tissue, such as, but not limited to, a viral skin lesion, such as, but not limited to, a viral wart, while preserving a basic architecture of the external hyperplastic tissue rather than dissolution of hydrolysis of protein peptide bonds of the external hyperplastic tissue, thereby providing a timely regeneration of healthy skin tissue after the external hyperplastic tissue has been treated with the topical composition, and thereby contributing to less damage to surrounding healthy skin tissue, as a result of, destructive potential of the topical composition being effectively neutralized and penetration of the topical composition into the surrounding healthy tissue being effectively blocked. The topical composition is a liquid and includes a caustic portion and a detoxifying and cleansing portion. The caustic portion is a liquid and has a caustic effect on the external hyperplastic tissue. The detoxifying and cleansing portion is a white activated charcoal powder for having a detoxifying and cleansing effect on the external hyperplastic tissue and having silicon dioxide as an active substance.

The novel features considered characteristic of the embodiments of the present invention are set forth in the appended claims. The embodiments of the present invention themselves, however, both as to their construction and to their method of operation, together with additional objects and advantages thereof, will be best understood from the following description of the embodiments of the present invention when read and understood in connection with the accompanying figures of the drawing.

BRIEF DESCRIPTION OF THE FIGURES OF THE DRAWING

The figures of the drawing are briefly described as follows:

FIG. 3 is a table of the ingredients and their respective concentrations given in wt/vol % of the caustic portion of the topical composition of the embodiments of the present invention;

FIGS. 5A-5H are a table and photographs of a single external hyperplastic tissue on the frown area of the forehead of a patient, which is being treated with the topical composition of the embodiments of the present invention, wherein:

FIG. 5A is a table of assessment data tabulated prior to application of the topical composition of the embodiments of the present invention;

FIG. 5B is a photograph taken three minutes after application of the topical composition of the embodiments of the present invention, along with tabulated associated assessment data;

FIG. 5C is a photograph taken eight minutes after application of the topical composition of the embodiments of the present invention, along with tabulated associated assessment data;

FIG. 5D is a photograph taken fifteen minutes after application of the topical composition of the embodiments of the present invention, along with tabulated associated assessment data;

FIG. 5E is a photograph taken eight hours after application of the topical composition of the embodiments of the present invention, along with tabulated associated assessment data;

FIG. 5F is a photograph taken six days after application of the topical composition of the embodiments of the present invention, along with tabulated associated assessment data;

FIG. 5G is a photograph taken eight days after application of the topical composition of the embodiments of the present invention, along with tabulated associated assessment data; and FIG. 5H is a photograph taken fourteen days after application of the topical composition of the embodiments of the present invention, along with tabulated associated assessment data;

FIGS. 6A-6C are photographs of a pair of external hyperplastic tissues on the forehead of a patient, which are being treated with the topical composition of the embodiments of the present invention, wherein:

FIG. 6A is a photograph taken prior to application of the topical composition of the embodiments of the present invention;

FIG. 6B is a photograph taken three days after application of the topical composition of the embodiments of the present invention; and FIG. 6C is a photograph taken eight days after application of the topical composition of the embodiments of the present invention;

FIGS. 7A-7D are photographs of a single external hyperplastic tissue on the chin of a patient, which is being treated with the topical composition of the embodiments of the present invention, wherein:

FIG. 7A is a photographs taken five minutes after application of the topical composition of the embodiments of the present invention;

FIG. 7B is a photographs taken three days after application of the topical composition of the embodiments of the present invention;

FIG. 7C is a photographs taken six days after application of the topical composition of the embodiments of the present invention; and FIG. 7D is a photographs taken three weeks after application of the topical composition of the embodiments of the present invention;

FIGS. 8A-8C are photographs of a single external hyperplastic tissue on the phalanx of the fourth finger of a patient, which is being treated with the topical composition of the embodiments of the present invention, wherein:

FIG. 8A is a photograph taken prior to application of the topical composition of the embodiments of the present invention;

FIG. 8B is a photograph taken fifteen minutes after application of the topical composition of the embodiments of the present invention; and FIG. 8C is a photograph taken two months after application of the topical composition of the embodiments of the present invention;

FIGS. 9A and 9B are photographs of six external hyperplastic tissues on the base of the thumb of a patient, which are being treated with the topical composition of the embodiments of the present invention, wherein:

FIG. 9A is a photograph taken prior to application of the topical composition of the embodiments of the present invention; and FIG. 9B is a photograph taken two months after application of the topical composition of the embodiments of the present invention;

FIGS. 10A and 10B are photographs of a plurality of external hyperplastic tissues on the heel of a patient, which are being treated with the topical composition of the embodiments of the present invention, wherein:

FIG. 10A is a photograph taken prior to application of the topical composition of the embodiments of the present invention; and FIG. 10B is a photograph taken one month after application of the topical composition of the embodiments of the present invention;

FIGS. 11A and 11B are photographs of three external hyperplastic tissues on the left side of the face of a patient, which are being treated with the topical composition of the embodiments of the present invention, wherein:

FIG. 11A is a photograph taken prior to application of the topical composition of the embodiments of the present invention; and FIG. 11B is a photograph taken three weeks after application of the topical composition of the embodiments of the present invention;

FIG. 12 is a table revealing the correlation between the size of the warts and their locations prior to application of the topical composition of the embodiments of the present invention;

FIG. 13 is a diagrammatic representation of the temperatures taken at the wart and at the surrounding area of the wart, subsequent to application of the topical composition of the embodiments of the present invention;

FIG. 14 is a table summarizing the temperature differences shown in FIG. 13; and FIGS. 15A-15B are photographs of three external hyperplastic tissues on the forearm of a patient, which are being treated with the topical composition of the embodiments of the present invention, wherein:

FIG. 15A is a photograph taken prior to application of the topical composition of the embodiments of the present invention; and FIG. 15B is a photograph taken fifteen days after application of the topical composition of the embodiments of the present invention.

LIST OF REFERENCE NUMERALS UTILIZED IN THE FIGURES OF THE DRAWING

Introductory

FIG. 1

Figure 1:
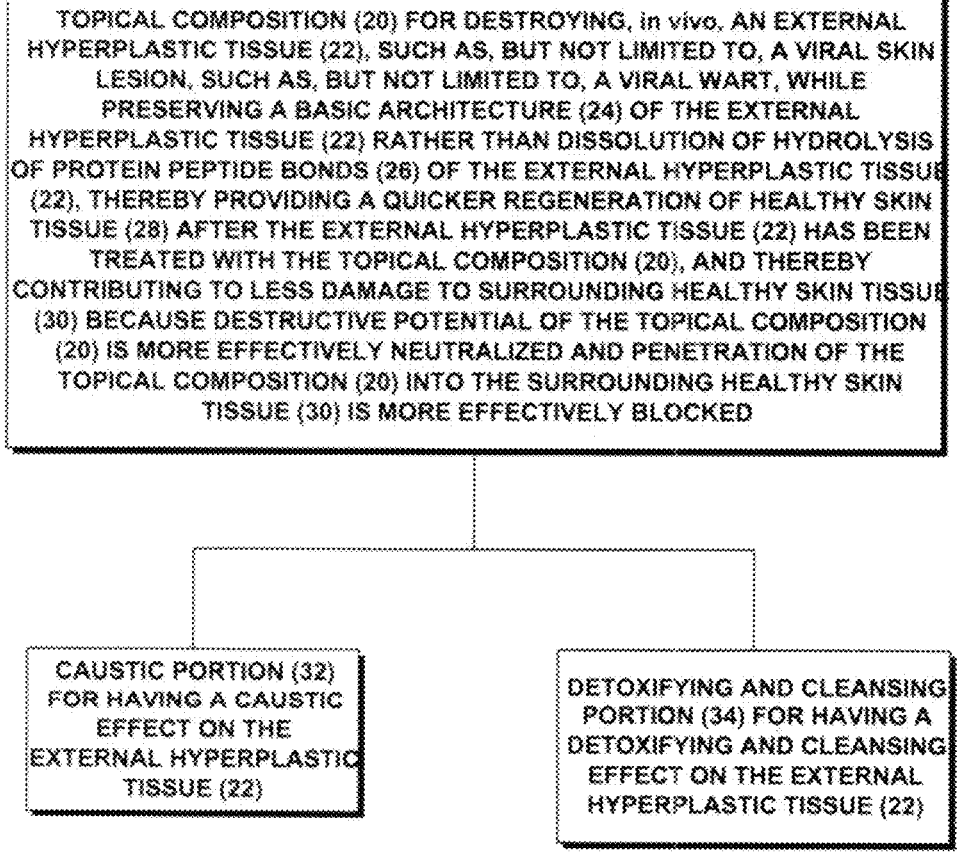
FIG. 1 is a block diagram of the overall topical composition of the embodiments of the present invention.
Figure 2A:
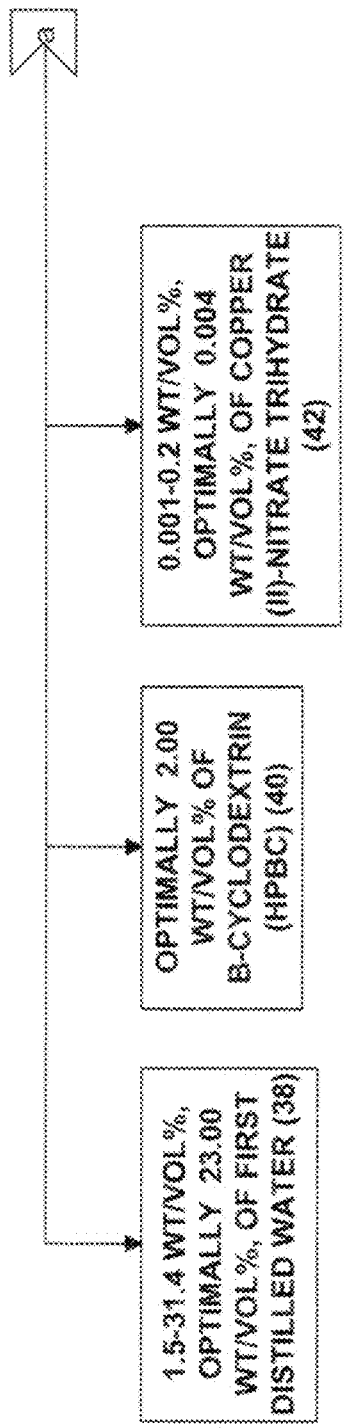
FIG. 2A-2D are a block diagram of the caustic portion of the topical composition of the embodiments of the present invention.
Figure 2B:
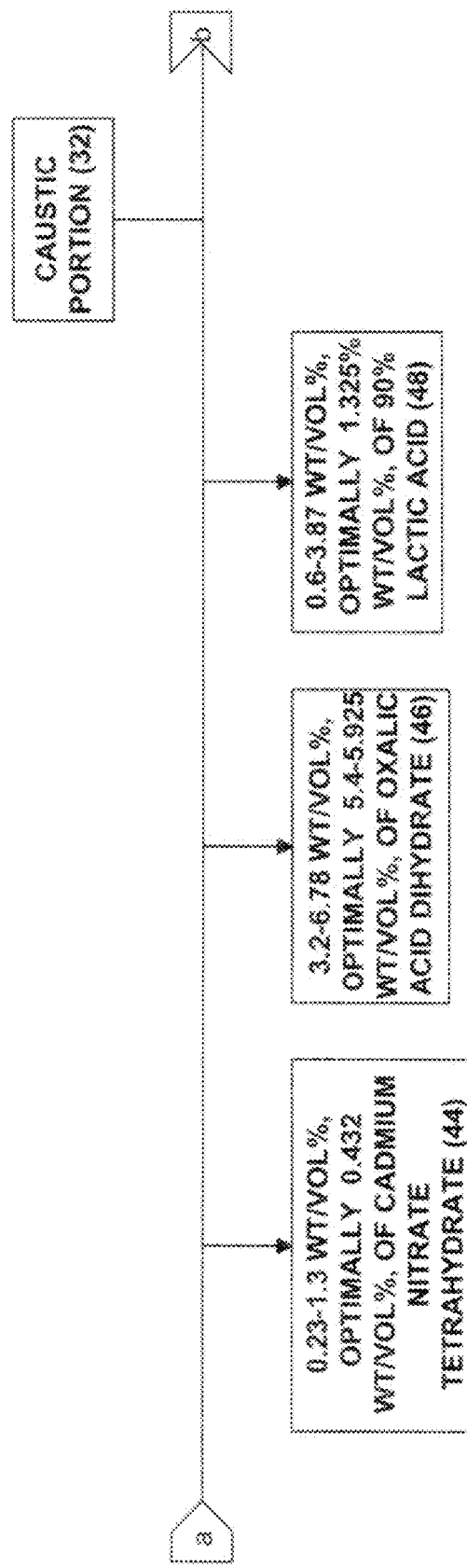
Figure 2C:
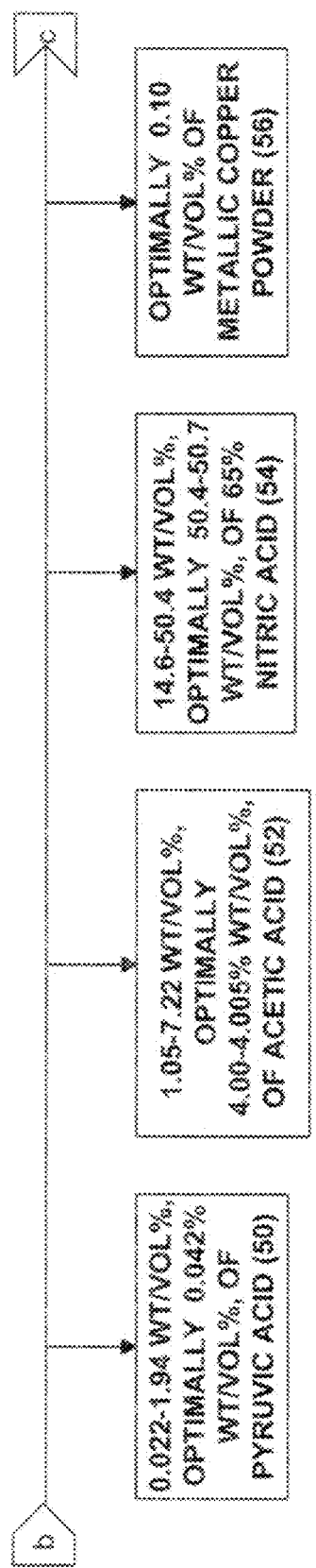
Figure 2D:
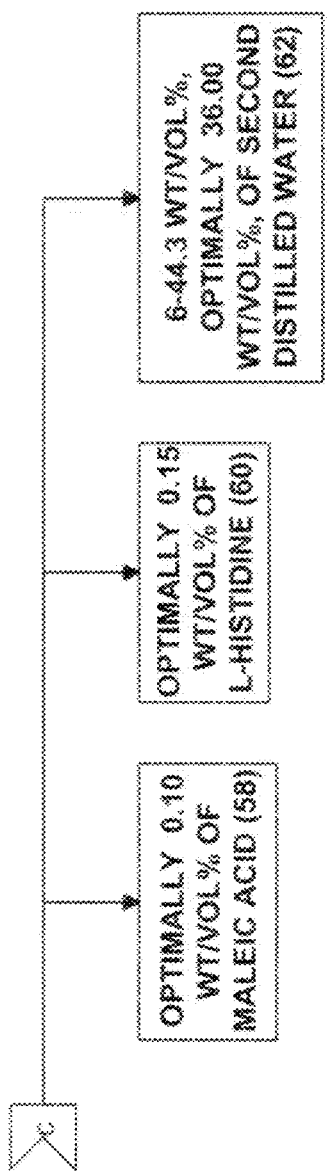

20 topical composition of embodiments of present invention for destroying, in vivo, external hyperplastic tissue 22, such as, but not limited to, viral skin lesion, such as, but not limited to, viral wart, while preserving basic architecture 24 of external hyperplastic tissue 22 rather than dissolution of hydrolysis of protein peptide bonds 26 of external hyperplastic tissue 22, thereby providing timely regeneration of healthy skin tissue 28 after external hyperplastic tissue 22 has been treated with topical composition 20, and thereby contributing to less damage to surrounding healthy skin tissue 30, as a result of, destructive potential of topical composition 20 being effectively neutralized and penetration of topical composition 20 into surrounding healthy tissue 30 being effectively blocked

22 external hyperplastic tissue, such as, but not limited to, viral skin lesion, such as, but not limited to, viral wart

24 basic architecture of external hyperplastic tissue 22

26 protein peptide bonds of external hyperplastic tissue 22

28 healthy skin tissue

30 surrounding healthy skin tissue

Overall Composition of Topical Composition 20

FIG. 1

32 caustic portion for having caustic effect on external hyperplastic tissue 22

34 detoxifying and cleansing portion for having detoxifying and cleansing effect on external hyperplastic tissue 22

Specific Composition of Caustic Portion 32

FIGS. 2A-2D and 3

38 1.5-31.4 wt/vol %—optimally 23.00 wt/vol %—of first distilled water

40 optimally 2.00 wt/vol % of b-cyclodextrin (HPBC)

42 0.001-0.2 wt/vol %—optimally 0.004 wt/vol %—of copper (II)-nitrate trihydrate

44 0.23-1.30 wt/vol %—optimally 0.432 wt/vol %—of cadmium nitrate tetrahydrate

46 3.2-6.78 wt/vol %—optimally 5.4-5.925 wt/vol %—of oxalic acid dihydrate

48 0.6-3.87 wt/vol %—optimally 1.325% wt/vol %—of 90% lactic acid

50 0.022-1.94 wt/vol %—optimally 0.042% wt/vol %—of pyruvic acid

52 1.05-7.22 wt/vol %—optimally 4.00-4.005% wt/vol %—of acetic acid

54 14.6-50.4 wt/vol %—optimally 50.4-50.7 wt/vol %—of 65% nitric acid

56 optimally 0.10 wt/vol % of metallic copper powder

58 optimally 0.10 wt/vol % of maleic acid

60 optimally 0.15 wt/vol % of L-histidine

62 8.6-44.3 wt/vol %—optimally 36.00 wt/vol %—of second distilled water

Specific Composition of Detoxifying and Cleansing Portion 34

FIG. 4

64 white activated charcoal powder for successfully coping with detoxifying intervention area and timely regeneration

66 silicon dioxide of white activated charcoal powder 64 for absorbing pathogenic microflora, for providing pronounced antimicrobial effect by promoting movement of toxic products from tissues, as result of, concentration and osmotic gradients followed by binding and excretion from body, for not decomposing in organic solvents and biological fluids, and for not accumulating in body

67 microcrystalline cellulose of white activated charcoal powder 64

DETAILED DESCRIPTION OF THE PREFERRED EMBODIMENTS

Introductory

Referring now to the figures of the drawing, in which like numerals indicate like parts, and particularly to FIG. 1, the topical composition of the embodiments of the present invention is shown generally at 20 for destroying, in vivo, an external hyperplastic tissue 22, such as, but not limited to, a viral skin lesion, such as, but not limited to, a viral wart, while preserving a basic architecture 24 of the external hyperplastic tissue 22 rather than dissolution of hydrolysis of protein peptide bonds 26 of the external hyperplastic tissue 22, thereby providing a timely regeneration of healthy skin tissue 28 after the external hyperplastic tissue 22 has been treated with the topical composition 20, and thereby contributing to less damage to surrounding healthy skin tissue 30, as a result of, destructive potential of the topical composition 20 being effectively neutralized and penetration of the topical composition 20 into the surrounding healthy skin tissue 30 being effectively blocked. Tissue regeneration is a genetically determinate process.

Overall Composition of the Topical Composition 20

The topical composition 20 encompasses a topical antiviral liquid for treatment of viral warts. The topical composition 20 is a multi-component formula that contains a number of acids and salts in an aqueous solution, and which has been shown to have superior effectiveness in completely penetrating and removing viral warts tissue, while encouraging timely regeneration of the healthy skin tissue 28. The topical composition 20 is not limited to treatment of viral warts and may be directed to any form of the external hyperplasic tissue 22.

The topical composition 20 contains a complex of halogenated and polymerized carboxylic acids and certain salts of microelements incorporated into a primary liquid delivery system. The salts may be halogenated salts, which are hydrocarbon salts in which at least one hydrogen atom is replaced by a halogen atom, such as, chlorine. The polymers are polymers of carboxylic acids that may be present, polymerization is a form where smaller molecules react with each other to form larger structural units, usually, polymers. The topical composition 20 destroys, in vivo, the external hyperplastic tissue 22, with morphological form of the external hyperplastic tissue 22 not mattering.

The mechanism of action of the topical composition 20 is based largely on oxidation and certain other chemical reactions of carboxylic acids and their intermediate reduction products used in balanced ratios and in relatively low concentrations.

Specifically, the overall composition of the topical composition 20 can best be seen in FIG. 1, and as such, will be discussed with reference thereto.

The topical composition 20 is a liquid and comprises a caustic portion 32 and a detoxifying and cleansing portion 34. The caustic portion 32 has a caustic effect on the external hyperplastic tissue 22. The detoxifying and cleansing portion 34 has a detoxifying and cleansing effect on the external hyperplastic tissue 22.

The caustic effect on the external hyperplastic tissue 22 causes a necrotic process to occur, followed by rejection of scab and cleaning of the intervention area. The necrotic process is initiated by the acids included in the topical composition 20, begins immediately after application of the topical composition 20, and is accompanied by an inflammatory reaction and the release of necrosis and inflammation by-products. These by-products themselves are a source of additional irritation and local intoxication. Their presence significantly slows down recovery and regeneration process, which can contribute to scarring. Therefore, the timely removal and neutralization of the necrotic and the inflammatory debris is an important and significant step in the treatment.

Specific Composition of the Caustic Portion 32

The specific composition of the caustic portion 32 can best be seen in FIGS. 2A-2D and 3, and as such, will be discussed with reference thereto.

The caustic portion 32 comprises:
1.5-31.4 wt/vol %—optimally 23.00 wt/vol %—of a first distilled water 38;
Optimally 2.00 wt/vol % of b-cyclodextrin (HPBC) 40;
0.001-0.2 wt/vol %—optimally 0.004 wt/vol %—of copper (II)-nitrate trihydrate 42;
0.23-1.3 wt/vol %—optimally 0.432 wt/vol %—of cadmium nitrate tetrahydrate 44;
3.2-6.78 wt/vol %—optimally 5.4-5.925 wt/vol %—of oxalic acid dehydrate 46;
0.6-3.87 wt/vol %—optimally 1.325% wt/vol %—of lactic acid (90%) 48;
0.022-1.94 wt/vol %—optimally 0.042% wt/vol %—of pyruvic acid 50;
1.05-7.22 wt/vol %—optimally 4.00-4.005% wt/vol %—of acetic acid 52;
14.6-50.4 wt/vol %—optimally 50.4-50.7 wt/vol %—of nitric acid (65%) 54;
Optimally 0.10 wt/vol % of metallic copper powder 56;
Optimally 0.10 wt/vol % of maleic acid 58;
Optimally 0.15 wt/vol % of 1-histidine 60; and
8.6-44.3 wt/vol %—optimally 36.00 wt/vol %—of a second distilled water 62.

For the readers' convenience, the ingredients of the caustic portion 32 discussed, supra, are tabulated in FIG. 3.

The b-cyclodextrin (HPBC) 40 of the caustic portion 32 is one of the ingredients in creating a primary delivery system that delivers the topical composition 20 to the external hyperplastic tissue 22 and combines all active ingredients of the topical composition 20, as a result of, its excellent incorporating ability.

The metallic copper powder 56 of the caustic portion 32 stabilizes and reduces intensity of decomposition of the oxalic acid dehydrate 46 of the caustic portion 32, the lactic acid 48 of the caustic portion 32, the pyruvic acid 50 of the caustic portion 32, the acetic acid 52 of the caustic portion 32, and the nitric acid 54 of the caustic portion 32, reduces activity loses of the caustic portion 32, is used in relatively small concentrations, and effectively neutralizes destruction potential.

The maleic acid 58 of the caustic portion 32 is another ingredient in creating the primary delivery system that delivers the topical composition 20 to the external hyperplastic tissue 22, provides a fast incorporation of ingredients into the b-cyclodextrin 40, and is used in relatively small concentrations.

The l-histidine 60 of the caustic portion 32 provides protection of the external hyperplastic tissue 22 from deep chemical burns, provides timely regeneration of the healthy skin tissue 28 after the external hyperplastic tissue 22 has been treated with the topical composition 20, helps to restore the healthy skin tissue 28 after the external hyperplastic tissue 22 has been treated with the topical composition 20 from action of acids, and does not decompose in acidic environments.

The cadmium nitrate tetrahydrate 44 of the caustic portion 32 is used in combination with the copper nitrate trihydrate 42 of the caustic portion 32 to stabilize the caustic action of the acids of the topical composition 20. The cadmium nitrate tetrahydrate 44 of the caustic portion 32 has an optimum concentration of 0.432%.

Specific Composition of the Detoxifying and Cleansing Portion 34

Figure 4:
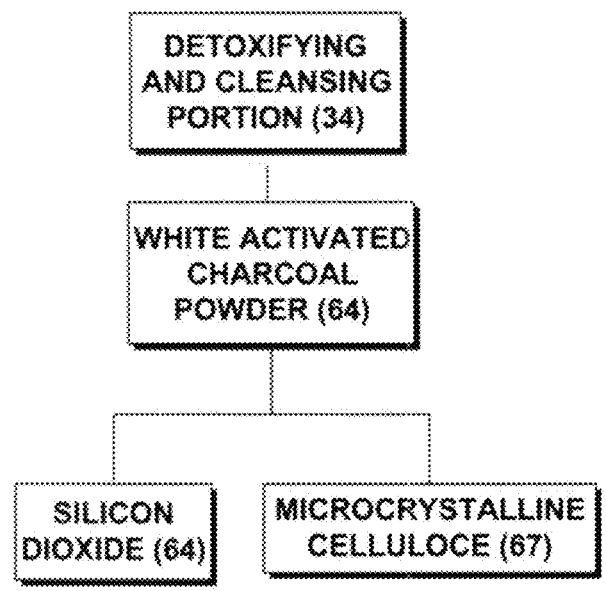
FIG. 4 is a block diagram of the detoxifying and cleansing portion of the topical composition of the embodiments of the present invention.

The specific composition of the detoxifying and cleansing portion 34 can best be seen in FIG. 4, and as such, will be discussed with reference thereto.

The detoxifying and cleansing portion 34 comprises a white activated charcoal powder 64 that is 10% of the topical composition 20, has silicon dioxide 66 as an active substance and further has microcrystalline cellulose 67, and successfully copes with detoxifying intervention area and speeding up regeneration process. The silicon dioxide 66 of the white activated charcoal powder 64 of the detoxifying and cleansing portion 34 has a large density, an absorption capacity, and a non-porous structure.

The large dispersity of the silicon dioxide 66 of the white activated charcoal powder 64 of the detoxifying and cleansing portion 34 provides a large active sorption surface, and consequently, the sorption capacity of the silicon dioxide 66 of the white activated charcoal powder 64 of the detoxifying and cleansing portion 34. The non-porous structure of the silicon dioxide 66 of the white activated charcoal powder 64 of the detoxifying and cleansing portion 34 ensures a high sorption rate.

The silicon dioxide 66 of the white activated charcoal powder 64 of the detoxifying and cleansing portion 34 has a significant adsorption activity with respect to substances of a protein nature, and promotes removal from the body of exo- and endo-toxins, toxic products of incomplete decomposition of large organic compounds, pathogenic antigens, and allergens of microbial or other origin. As a result of the presence on the surface of microorganisms of various protein structures, highly dispersed silicon dioxide 66 of the white activated charcoal powder 64 of the detoxifying and cleansing portion 34 actively absorbs pathogenic microflora, up to 1010 microbial bodies per 1 g. of the substance, and provides a pronounced antimicrobial effect.

The silicon dioxide 66 of the white activated charcoal powder 64 of the detoxifying and cleansing portion 34 promotes movement of toxic products from tissues, including medium molecules, oligopeptides, amines, and other substances, as a result of, concentration and osmotic gradients followed by binding and excretion from the body. The silicon dioxide 66 of the white activated charcoal powder 64 of the detoxifying and cleansing portion 34 has pronounced adsorption properties for phospholipids, monosaccharides, and proteins, 300-600 mg per 1 g. of sorbent, containing a primary amino group.

The silicon dioxide 66 of the white activated charcoal powder 64 of the detoxifying and cleansing portion 34 exhibits chemical and microbiological stability. It does not decompose in organic solvents and biological fluids, the structure of its particles does not change when pH changes, and it does not accumulate in the body. More than 99% of the silicon dioxide 66 of the white activated charcoal powder 64 of the detoxifying and cleansing portion 34 is excreted unchanged from tissues.

The microcrystalline cellulose 67 of the white activated charcoal powder 64 of the detoxifying and cleansing portion 34 complements the adsorption properties of the silicon dioxide 66 of the white activated charcoal powder 64 of the detoxifying and cleansing portion 34 by binding heavy metals.

CASE STUDY EXAMPLES

Example 1

Ten patients with viral warts were treated with only the caustic portion 32 of the topical composition 20—Group 1, and 10 patients with viral warts were treated with both the caustic portion 32 of the topical composition 20 and the detoxifying and cleansing portion 34 of the topical composition 20—Group 2. Results showed that tissue repair—regeneration—occurred three (3) times faster in Group 2 than in Group 1, as a result of, the topical composition 20.

Example 2

Treatment with the topical composition 20 of one skin wart on the frown area of the forehead of a patient can best be seen in FIGS. 5A-5H, and as such, will be discussed with reference thereto.

Referring to FIG. 5A, assessment of the one skin wart prior to utilization of the topical composition 20, reveals:
The size of the one skin wart is 5 mm×5 mm;
The color of the one skin wart and the color change of the one skin wart after utilization of the topical composition 20 is skin color;
No existence of cracks, scratches, calluses, etc. at the one skin wart;
No existence of inflammation—i.e., redness—at the one skin wart;
No existence of hemorrhages at the one skin wart;
No existence of pigmentation at the one skin wart; and
No existence of pain—or excessive sensitivity—at the one skin wart.

Referring further to FIG. 5A, assessment of the surrounding skin prior to treatment, reveals:
No cracks, scratches, calluses, etc. at the surrounding skin;

No existence of inflammation—i.e., redness—at the surrounding skin;
No existence of hemorrhages at the surrounding skin; and
No existence of pigmentation at the surrounding skin.

Referring to FIG. 5B, assessment of the one skin wart at three minutes after utilization of the topical composition 20, reveals:
The size of the one skin wart is 5 mm×5 mm;
The color of the one skin wart and the color change of the one skin wart after utilization of the topical composition 20 is white;
No existence of cracks, scratches, calluses, etc. at the one skin wart;
No existence of inflammation—i.e., redness—at the one skin wart;
No existence of hemorrhages at the one skin wart;
No existence of pigmentation at the one skin wart; and
No existence of pain—or excessive sensitivity—at the one skin wart.

Referring further to FIG. 5B, assessment of the surrounding skin at three minutes after treatment, reveals:
No existence of cracks, scratches, calluses, etc. at the surrounding skin;
No existence of inflammation—i.e., redness—at the surrounding skin;
No existence of hemorrhages at the surrounding skin; and
No existence of pigmentation at the surrounding skin.

Referring to FIG. 5C, assessment of the one skin wart at eight minutes after utilization of the topical composition 20, reveals:
The size of the one skin wart is 5 mm×5 mm;
The color of the one skin wart and the color change of the one skin wart after utilization of the topical composition 20 is white—gray;
No existence of cracks, scratches, calluses, etc. at the one skin wart;
No existence of inflammation—i.e., redness—at the one skin wart;
No existence of hemorrhages at the one skin wart;
No existence of pigmentation at the one skin wart; and
Noexistence of pain—or excessive sensitivity—at the one skin wart.

Referring further to FIG. 5C, assessment of the surrounding skin at eight minutes after treatment, reveals:
No existence of cracks, scratches, calluses, etc. at the surrounding skin;
Existence of perifocal inflammation—i.e., redness—at the surrounding skin;
No existence of hemorrhages at the surrounding skin; and
No existence of pigmentation at the surrounding skin.

Referring to FIG. 5D, assessment of the one skin wart at fifteen minutes after utilization of the topical composition 20 reveals:
The size of the one skin wart is 5 mm×5 mm;
The color of the one skin wart and the color change of the one skin wart after utilization of the topical composition 20 is gray;
No existence of cracks, scratches, calluses, etc. at the one skin wart;
No existence of inflammation—i.e., redness—at the one skin wart;
No existence of hemorrhages at the one skin wart;
No existence of pigmentation at the one skin wart; and
No existence of pain—or excessive sensitivity—at the one skin wart.

Referring further to FIG. 5D, assessment of the surrounding skin at fifteen minutes after treatment, reveals:
No existence of cracks, scratches, calluses, etc. at the surrounding skin;
Existence of perifocal inflammation,—i.e., redness—at the surrounding skin;
No existence of hemorrhages at the surrounding skin; and
No existence of pigmentation at the surrounding skin.

Referring to FIG. 5E, assessment of the one skin wart at eight hours after utilization of the topical composition 20, reveals:
The size of the one skin wart is 5 mm×5 mm;
The color of the one skin wart and the color change of the one skin wart after utilization of the topical composition 20 is brown;
No existence of cracks, scratches, calluses, etc. at the one skin wart;
No existence of inflammation—i.e., redness—at the one skin wart;
No existence of hemorrhages at the one skin wart
No existence of pigmentation at the one skin wart; and
No existence of pain—or excessive sensitivity—at the one skin wart.

Referring further to FIG. 5E, assessment of the surrounding skin at eight hours after treatment, reveals:
No existence of cracks, scratches, calluses, etc. at the surrounding skin;
Existence of perifocal inflammation—i.e., redness—at the surrounding skin;
No existence of inflammation—i.e., redness—at the surrounding skin;
No existence of hemorrhages at the surrounding skin; and
No existence of pigmentation at the surrounding skin.

Referring to FIG. 5F, assessment of the one skin wart at six days after utilization of the topical composition 20, reveals:
The size of the one skin wart to be 5 mm×5 mm;
The color of the one skin wart and the color change of the one skin wart after utilization of the topical composition 20 is pink;
No existence of cracks, scratches, calluses, etc. at the one skin wart;
No existence of inflammation—i.e., redness—at the one skin wart;
No existence of hemorrhages at the one skin wart;
No existence of pigmentation at the one skin wart; and
No existence of pain—or excessive sensitivity—at the one skin wart.

Referring further to FIG. 5F, assessment of the surrounding skin at six days after treatment, reveals:
No existence of cracks, scratches, calluses, etc. at the surrounding skin;
Existence of inflammation—i.e., pink—at the surrounding skin;
No existence of hemorrhages at the surrounding skin; and
No existence of pigmentation at the surrounding skin.

Figure 5G:
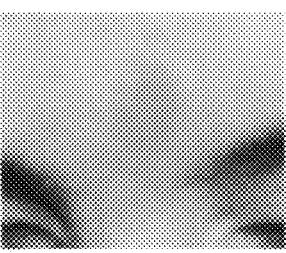

Referring to FIG. 5G, assessment of the one skin wart at eight days after utilization of the topical composition 20, reveals
The size of the one skin wart is 5 mm×5 mm;
The color of the one skin wart and the color change of the one skin wart after utilization of the topical composition 20 is pink;
No existence of cracks, scratches, calluses, etc. at the one skin wart;
No existence of inflammation—i.e., redness—at the one skin wart;

No existence of hemorrhages at the one skin wart;
No existence of pigmentation at the one skin wart; and
No existence of pain—or excessive sensitivity—at the one skin wart.

Referring further to FIG. 5G, assessment of the surrounding skin at eight days after treatment, reveals:
No existence of cracks, scratches, calluses etc. at the surrounding skin;
No existence of inflammation—i.e., redness—at the surrounding skin;
No existence of hemorrhages at the surrounding skin; and
No existence of pigmentation at the surrounding skin.

Figure 5H:
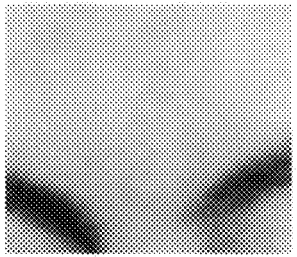

Referring to FIG. 5H, assessment of the one skin wart at fourteen days after utilization of the topical composition 20, reveals:
The size of the one skin wart is 5 mm×5 mm;
The color of the one skin wart and the color change of the one skin wart after utilization of the topical composition 20 is skin color;
No existence of cracks, scratches, calluses, etc. at the one skin wart;
No existence of inflammation—i.e., redness—at the one skin wart;
No existence of hemorrhages at the one skin wart;
No existence of pigmentation at the one skin wart; and
No existence of pain or excessive sensitivity at the one skin wart.

Referring further to FIG. 5H, assessment of the surrounding skin at eight days after treatment, reveals:
No existence of cracks, scratches, calluses etc. at the surrounding skin;
No existence of inflammation—i.e., redness—at the surrounding skin;
No existence of hemorrhages at the surrounding skin; and
No existence of pigmentation at the surrounding skin.

Example 3

Treatment with the topical composition 20 of two skin warts on the forehead of a 37 year old male patient can best be seen in FIGS. 6A-6C, and as such, will be discussed with reference thereto.

Figures 6A, 6B, 6C:
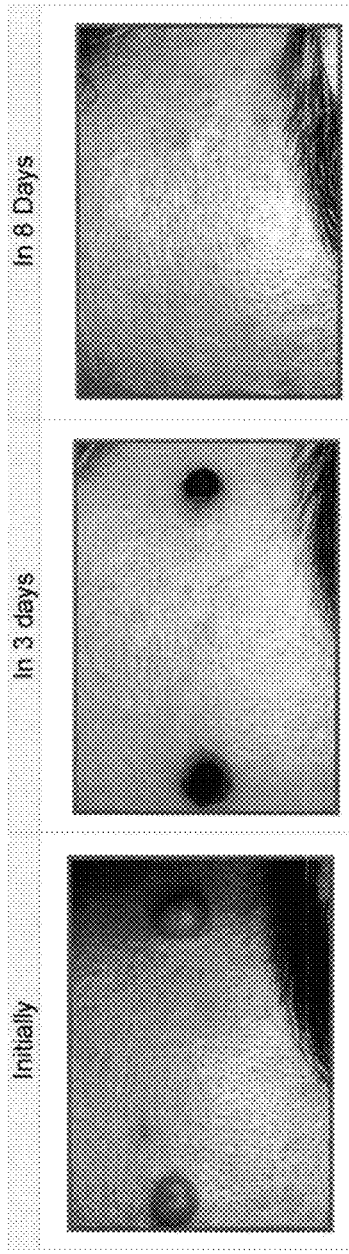

Referring to FIG. 6A, assessment of the two skin warts prior to treatment, reveals size of the two skin warts to be 5 mm and 6 mm, respectively. The topical composition 20 was applied to the two skin warts, once by a capillary applicator. Referring to FIG. 6B, at the end of day three, the two skin warts became mummified[12], and referring to FIG. 6C, at day eight, the surface of the patient's skin was completely cleared of the two skin warts.

[12]Mummification occurs when the tissue viability is lost, but the anatomical structure is largely retained, i.e., the tissue is fixed intravitally.

Example 4

The treatment with the topical composition 20 of a wart on the chin of a 29 year old female can best be seen in FIGS. 7A-7D, and as such, will be discussed with reference thereto.

Referring to FIG. 7A, assessment of the wart prior to treatment, reveals size of the wart is 10 mm. The topical composition 20 was applied to the wart, by alternating cycles with 5 minute intervals. Further referring to FIG. 7A, in five minutes, the wart became whitish gray. Referring to FIG. 7B, at day three, the wart became mummified.

Referring to FIG. 7C, at day six, the wart was almost ready to shed. At day 9, the mummified wart shed out. Referring to FIG. 7D, at three weeks, the surface of the patient's skin was completely cleared of the wart.

Example 5

The treatment with the topical composition 20 of a keratinized wart on the phalanx of the fourth finger of a 46 year old female can best be seen in FIGS. 8A-8C, and as such, will be discussed with reference thereto.

Figures 8A, 8B, 8C:
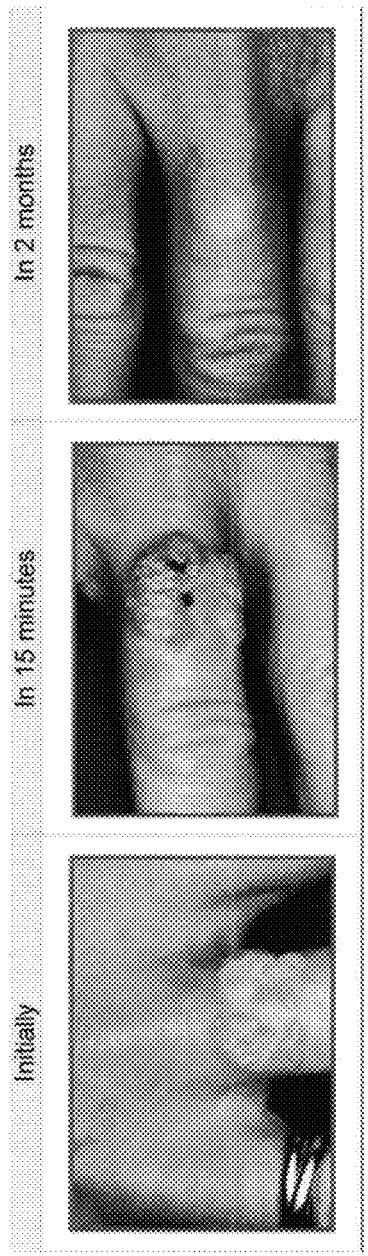

Referring to FIG. 8A, assessment of the wart prior to treatment, reveals the size of the keratinized wart is 12 mm. The topical composition 20 was applied to the keratinized wart by alternating 4 cycles with 5 minute intervals. Referring to FIG. 8B, in fifteen minutes, the keratinized wart became whitish gray. At day five, the keratinized wart became mummified. At day 10, the mummified keratinized wart was about to shed. On day 14, the mummified wart shed out. Referring to FIG. 8C, at two months, the surface of the patient's skin was completely cleared of the wart.

Example 6

The treatment with the topical composition 20 of six warts at the base of the thumb of a 16 year old male can best be seen in FIGS. 9A and 9B, and as such, will be discussed with reference thereto.

Figures 9A, 9B:
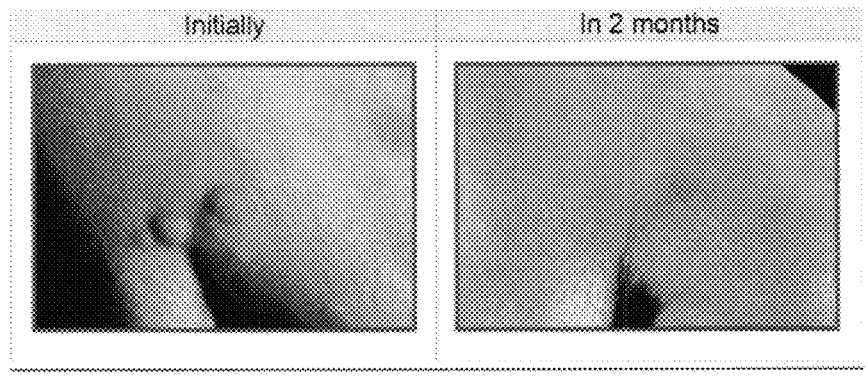

Referring to FIG. 9A, assessment of the six warts prior to treatment, reveals the sizes of the six warts were as follows: two warts were 5 mm and 4 warts were 2 mm. The topical composition 20 was applied to the six warts. Referring to FIG. 9B, at one month, the six warts were resolved.

Example 7

The treatment with the topical composition 20 of plantar warts at the heel of the foot of a 54 year old male can best be seen in FIGS. 10A and 10B, and as such, will be discussed with reference thereto.

Figures 10A, 10B:
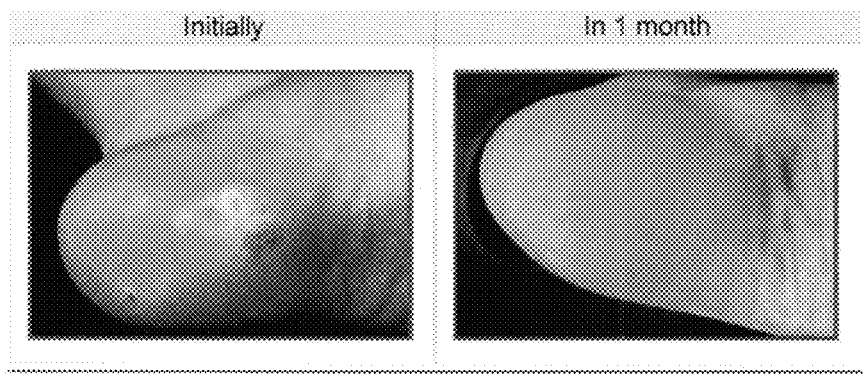

Referring to FIG. 10A, assessment of the six warts prior to treatment, reveals the sizes of the warts to be 3 to 10 mm. The topical composition 20 was applied to the warts by alternating five cycles with five min intervals. Referring to FIG. 10B, at one month, the six warts were resolved.

Example 8

The treatment with the topical composition 20 of three external hyperplastic tissues on the left side of the face of a 58 year old male can best be seen in FIGS. 11A and 11B, and as such, will be discussed with reference thereto.

Figures 11A, 11B:
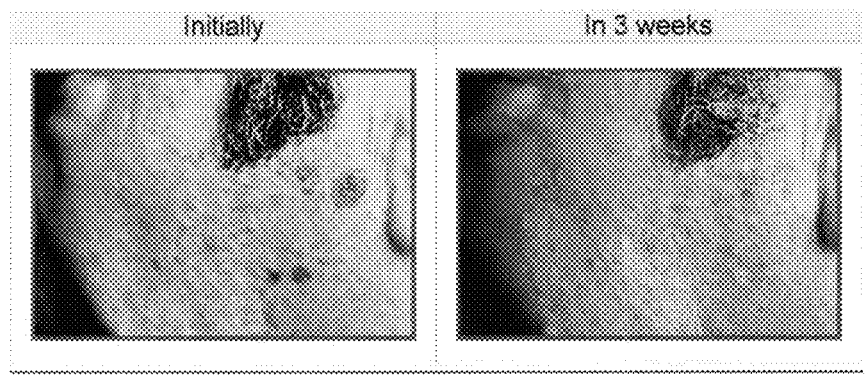

Referring to FIG. 11A, assessment of the three external hyperplastic tissues on the left side of the face of the patient, reveals the size of the warts to be one at 6 mm and 2 at mm. The topical composition 20 was applied to the warts during 15 days. Referring to FIG. 11B, after 3 weeks, all warts decreased twice in size.

Example 9

86 patients with skin viral warts were treated with the topical composition 20. Among the 86 patients treated were 54 females in an age range of 14-64 years old and 32 males in an age range of 15-55 years old.

Single warts were detected in 23 patients, two warts were detected in 24 patients, three warts were detected in 17 patients, and more than three warts were detected in 22 patients. All together 244 warts were treated. 64 warts had the size less than 1.0 mm, 99 warts had the size more than 1.0 up to 2.0 mm, 54 warts had the size more than 2.0 up to 3.0 mm, 18 warts had the size more than 3.0 up to 4.0 mm., and 9 warts had the size more than 4.0 up to 5.0 mm.

A table revealing the size of the warts and their locations can best be seen in FIG. 12.

The warts intended for treatment and the surrounding skin were carefully assessed prior to utilization of the topical composition 20 by the following parameters:

Assessment of the Wart

Exact location and amount of skin viral warts;
Size of each wart;
Condition of each wart, including:
  Integrity of the wart, such as, but not limited to, cracks, scratches, calluses, etc.;
  Existence of inflammation, such as, but not limited to, redness;
  Existence of hemorrhages;
  Existence of maceration or flakiness in wart;
  Existence of pigmentation; and
  Existence of pain—or excessive sensitivity—of the wart.

Assessment of Surrounding Skin

Condition of surrounding skin, including:
  Integrity of the surrounding skin, such as, but not limited to, cracks, scratches, calluses, etc.;
  Existence of inflammation, such as, but not limited to, redness;
  Existence of hemorrhages;
  Existence of skin irritation; and
  Existence of skin dyspigmentation.

The area of each of the warts, and their surrounding skin, were cleaned and degreased with alcohol. The topical composition 20 was carefully applied strictly to the wart by way of a special 0.8 mm or 0.5 mm., depending on the size of the wart, micro-hematocrit capillary glass applicator. The surface of treated wart was moistened. The number of applications and the time and intensity of subsequent skin reactions, discoloration of the wart, redness of surrounding skin, and burning sensation, depended on the type, size, and pigmentation of the wart. On average, about 0.025-0.05 ml of the tropical composition 20 was required per wart. No more than 5-6 warts were treated at one time and the total area of the procedure was not more than 4.0-5.0 square cm.

Additionally, the local temperature measurements were taken for all patients subsequent to utilization of the topical composition 20. The Amprobe TMD 90A digital thermometer was used. The measurements were taken at the wart itself, at the area of visually determined skin reaction redness around 3-4 cm from the area of the wart, and the intact skin at 6-7 cm from the area of the wart, are shown in FIG. 13 and as tabulated in FIG. 14.

Example 10

The treatment with the topical composition 20 of three warts on the forearm of a 32 year old male can best be seen in FIGS. 15A and 15B, and as such, will be discussed with reference thereto.

Figures 15A, 15B:

Referring to FIG. 15A, the sizes of the warts included one wart was up to 1.0 mm and two warts were up to 2.0 mm. The topical composition 20 was applied three times a day for 2 weeks.

At the end of day 10, the sizes of the warts decreased by up to 60-65%. Referring to FIG. 15B, at the end of day 15, the surface of patient's skin was completely cleared from existing warts.

Results Provided by the Topical Composition 20[13]

The topical composition 20 of the embodiments of the present invention provides at least the following results:

Utilization of natural active ingredients;

Eliminated from the skin after fulfilling the effect of its natural active ingredients;

Complete destruction of the external hyperplastic tissue 22;

Provides a stable composition, which is accomplished by the delivery system of the b-cyclodextrine 40 of the caustic portion 32;

Elimination of hydrolysis of protein peptide bonds of the external hyperplastic tissue 22, which is fulfilled by the nitric acid 54 of the caustic portion 32, the acetic acid 52 of the caustic portion 32, the pyruvic acid 50 of the caustic portion 32, the maleic acid 58 of the caustic portion 32, and the l-histidine 60 of the caustic portion 32;

Timely regeneration of healthy skin tissue 28 after the external hyperplastic tissue 22 has been treated with the topical composition 20, which is accomplished by the white activated charcoal powder 64 of the detoxifying and cleansing portion 34 and the l-histidine 60 of the caustic portion 32;

Prevention of damage to surrounding healthy skin tissue 30, which is accomplished by the delivery system of the b-cyclodextrine of the caustic portion 32;

Destruction potential is effectively neutralized, which is accomplished by the metallic copper 56 of the caustic portion 32;

Penetration of the topical composition 20 into the surrounding healthy tissue 30 is effectively blocked, which is accomplished by the delivery system, as a result of, the delivery system acting selectively only on targeted tissues;

Penetration inside of the external hyperplastic tissue 22, which is accomplished by the delivery system acting selectively only on targeted tissues;

Prevention of irritation of the skin;

Elimination of undesirable maceration, inflammatory, or coarse keratolytic process that can lead to the spread of the virus to other skin areas, which is accomplished by the links of one chain and fulfilled by the white activated charcoal powder 64 of the detoxifying and cleansing portion 34;

100% effectiveness proved by clinical observations;

Suitable utilization for all morphological and clinical types of external hyperplastic tissue, including non-malignant formations of the skin and different hyper plastic processes of the skin;

Elimination of pain during and after use, which is accomplished by the l-histidine 60 of the caustic portion 32 and the white activated charcoal powder 64 of the detoxifying and cleansing portion 34;

Elimination of clinical complications, which is accomplished by the combination of the delivery system and the white activated charcoal powder 64 of the detoxifying and cleansing portion 34;

Elimination of clinically proven virtual recurrences;

Elimination of post treatment cosmetic defects, such as, but not limited to, scars, keloids, hyper- or hypo-pigmentation, and other skin blemishes;

Elimination of side effects, which is accomplished by the combination of the delivery system and the white activated charcoal powder 64 of the detoxifying and cleansing portion 34;

Allowance of the patient to return to work or follow common daily regimes, such as, but not limited to, taking a shower, using makeup, and continuing a usual diet, etc. in 1-2 hours after utilization of the topical composition 20; and Elimination of sensitizing or allergic reactions, which is accomplished by the combination of all ingredients used. There is no extra-non-functional ingredient in the topical composition 20.

[13]*Ex parte Tanaka, Marushima and Takahashi,* 174 USPQ 38 ["Claims are not rejected . . . if the prior art devices do not accomplish applicant's result" [Emphasis added]; and In re Dillon, 919 F.2d 688, 692 (Fed. Cir. 1990) ["A prima facie case of . . . [unpatentability] requires that the prior art suggest the . . . problem the applicant attempts to solve." [Emphasis added].

Impressions

It will be understood that each of the elements described, supra—or two or more together—may also find a useful application in other types of compositions differing from the types described, supra.

While the embodiments of the present invention have been illustrated and described as embodied in a topical composition for destroying, in vivo, an external hyperplastic tissue, such as, but not limited to, a viral skin lesion, such as, but not limited to, a viral wart, while preserving a basic architecture of the external hyperplastic tissue rather than dissolution of hydrolysis of protein peptide bonds of the external hyperplastic tissue, thereby providing a timely regeneration of healthy skin tissue after the external hyperplastic tissue has been treated with the topical, and thereby contributing to less damage to surrounding healthy skin tissue, as a result of, destructive potential of the topical composition being effectively neutralized and penetration of the topical composition into the surrounding healthy tissue being effectively blocked, nevertheless, they are not limited to the details shown, since it will be understood that various omissions, modifications, substitutions, and changes in the forms and details of the topical composition of the embodiments of the present invention illustrated and their operation can be made by those skilled in the art without departing in any way from the spirit of the topical composition of the embodiments of the present invention.

Without further analysis, the foregoing will so fully reveal the gist of the topical composition of the embodiments of the present invention that others can by applying current knowledge readily adapt them for various applications without omitting features that from the standpoint of prior art fairly constitute characteristics of the generic or specific aspects of the topical composition of the embodiments of the present invention.

The invention claimed is:

1. A topical composition for destroying, in vivo, an external hyperplastic tissue, while preserving a basic architecture of the external hyperplastic tissue rather than dissolution of hydrolysis of protein peptide bonds of the external hyperplastic tissue, thereby providing a timely regeneration of healthy skin tissue after the external hyperplastic tissue has been treated with said topical composition, and thereby contributing to less damage to surrounding healthy skin tissue, as a result of, destructive potential of said topical composition being effectively neutralized and penetration of the topical composition into the surrounding healthy skin tissue being effectively blocked, said topical composition comprising:
   a) a caustic portion for having a caustic effect on the external hyperplastic tissue; and
   b) a detoxifying and cleansing portion for having a detoxifying and cleansing effect on the external hyperplastic tissue; and
   wherein said detoxifying portion comprises:
   i) white activated charcoal powder;
   ii) silicon dioxide; and
   iii) microcrystalline cellulose.

2. The topical composition of claim 1, wherein said topical composition:
   a) is a liquid;
   b) is a multi-component composition containing a number of acids and salts;
   c) is a complex of halogenated and polymerized carboxylic acids and salts of microelements incorporated into a primary liquid delivery system that delivers said topical composition to the external hyperplastic tissue; and
   d) destroys, in vivo, the external hyperplastic tissue, regardless of morphological form of the external hyperplastic tissue.

3. The topical composition of claim 2, wherein said salts are halogenated salts.

4. The topical composition of claim 2, wherein:
   a) said topical composition has a mechanism of action; and
   b) said mechanism of action of said topical composition is based on oxidation and chemical reactions of carboxylic acids and their intermediate reduction products used in balanced ratios and in low concentrations.

5. The topical composition of claim 2, wherein said caustic portion comprises:
   a) a first distilled water;
   b) b-cyclodextrine (HPBC);
   c) metallic copper powder;
   d) l-histidine; and
   e) a second distilled water.

6. The topical composition of claim 5, wherein:
   a) said first distilled water of said caustic portion is in an amount of 1.5-31.4 wt/vol %;
   b) said b-cyclodextrin (HPBC) of said caustic portion is in an amount of 2.00 wt/vol %;
   c) said metallic copper powder of said caustic portion is in an amount of 0.10 wt/vol %;
   d) said l-histidine of said caustic portion is in an amount of 0.15 wt/vol %; and
   e) said second distilled water of said caustic portion is in an amount of 8.6-44.3 wt/vol %.

7. The topical composition of claim 5, wherein:
   a) said first distilled water of said caustic portion is in an amount of 23.00 wt/vol %; and
   b) said second distilled water of said caustic portion is in an amount of 36.00 wt/vol %.

8. The topical composition of claim 5, wherein said caustic portion further comprises:
a) copper (II)-nitrate trihydrate;
b) cadmium nitrate tetrahydrate;
c) oxalic acid dihydrate;
d) lactic acid;
e) pyruvic acid;
f) acetic acid;
g) nitric acid; and
h) maleic acid.

9. The topical composition of claim 8, wherein:
a) said copper (II)-nitrate trihydrate of said caustic portion is in an amount of 0.001-0.2 wt/vol %;
b) said cadmium nitrate tetrahydrate of said caustic portion is in an amount of 0.23-1.3 wt/vol %;
c) said oxalic acid dehydrate of said caustic portion is in an amount of 3.2-6.78 wt/vol %;
d) said lactic acid of said caustic portion is in an amount of 0.6-3.87 wt/vol %;
e) said pyruvic acid of said caustic portion is in an amount of 0.022-1.94 wt/vol %;
f) said acetic acid of said caustic portion is in an amount of 1.05-7.22 wt/vol %;
g) said nitric acid of said caustic portion is in an amount of 14.6-72.45 wt/vol %; and
h) said maleic acid of said caustic portion is in an amount of 0.10 wt/vol %.

10. The topical composition of claim 8, wherein:
a) said copper (II)-nitrate trihydrate of said caustic portion is in an amount of 0.004 wt/vol %;
b) said cadmium nitrate tetrahydrate of said caustic portion is in an amount of 0.432 wt/vol %;
c) said oxalic acid dehydrate of said caustic portion is in an amount of 5.45-5.925 wt/vol %;
d) said lactic acid (90%) of said caustic portion is in an amount of 1.325 wt/vol %;
e) said pyruvic acid of said caustic portion is in an amount of 0.042 wt/vol %;
f) said acetic acid of said caustic portion is in an amount of 4.00-4.005 wt/vol %; and
g) nitric acid of said caustic portion is in an amount of 50.4-50.7 wt/vol %.

11. The topical composition of claim 5, wherein said b-cyclodextrin (HPBC) of said caustic portion:
a) creates said liquid primary delivery system; and
b) combines all active ingredients of said topical composition, as a result of, its incorporating ability.

12. The topical composition of claim 8, wherein said metallic copper powder of said caustic portion:
a) stabilizes and reduces intensity of decomposition of said oxalic acid dihydrate of said caustic portion, said lactic acid of said caustic portion, said pyruvic acid of said caustic portion, said acetic acid of said caustic portion, and said nitric acid of said caustic portion;
b) reduces activity loses of said caustic portion; and
c) effectively neutralizes destruction potential.

13. The topical composition of claim 8, wherein said maleic acid of said caustic portion:
a) creates said exact delivery system; and
b) provides a fast incorporation of ingredients into said b-cyclodextrin.

14. The topical composition of claim 5, wherein said l-histidine of said caustic portion:
a) provides protection of the external hyperplastic tissue from deep chemical burns;
b) helps to restore the healthy skin tissue after the external hyperplastic tissue has been treated with said topical composition from action of acids; and
d) does not decompose in acidic environments.

15. The topical composition of claim 5, wherein said l-histidine of said caustic portion and said white activated charcoal powder of said detoxifying and cleansing portion provide the timely regeneration of the healthy skin tissue after the external hyperplastic tissue has been treated with said topical composition.

16. The topical composition of claim 8, wherein said cadmium nitrate tetrahydrate of said caustic portion is used in combination with said copper nitrate trihydrate of said caustic portion to stabilize caustic action of acids of said topical composition.

17. The topical composition of claim 1, wherein said white activated charcoal powder of said detoxifying and cleansing portion:
a) is 10% of said topical composition;
b) successfully copes with detoxifying intervention area; and
c) provides timely regeneration.

18. The topical composition of claim 17, wherein said detoxifying and cleansing portion has:
a) a large dispersity;
b) an absorption capacity; and
c) a non-porous structure;
wherein said large dispersity of said silicon dioxide of said detoxifying and cleansing portion provides a large active sorption surface, and consequently, said absorption capacity of said silicon dioxide of said detoxifying and cleansing portion; and wherein said non-porous structure of said silicondioxide of said detoxifying and cleansing portion ensures a high sorption rate.

19. The topical composition of claim 17, wherein said silicon dioxide of said detoxifying and cleansing portion:
a) absorbs substances of a protein nature; and
b) promotes removal from the body of exo- and endo-toxins, toxic products of incomplete decomposition of large organic compounds, pathogenic antigens, and allergens of microbial or other origin.

20. The topical composition of claim 17, wherein said silicon dioxide of said detoxifying and cleansing portion:
a) actively absorbs pathogenic microflora—up to 1010 microbial bodies per 1 g. of said substance;
b) provides a pronounced antimicrobial effect;
c) promotes movement of toxic products from tissues, including medium molecules, oligopeptides, amines, and other substances, as a result of, concentration and osmotic gradients followed by binding and excretion from the body;
d) has adsorption properties for phospholipids, monosaccharides, and proteins 300-600 mg per 1 g. of sorbent containing a primary amino group;
e) exhibits chemical and microbiological stability;
f) does not decompose in organic solvents and biological fluids;
g) structure of its particles does not change when pH changes;
h) does not accumulate in the body; and
i) more than 99% is excreted unchanged from tissues.

21. The topical composition of claim 20, wherein said microcrystalline cellulose of said detoxifying and cleansing portion complements said adsorption properties of said silicon dioxide of said detoxifying and cleansing portion by binding heavy metals.

22. The topical composition of claim 8, wherein said topical composition:

a) is eliminated from the skin after fulfilling effect of its natural active ingredients;

b) provides a stable composition, which is accomplished by said delivery system of said b-cyclodextrine of said caustic portion; and c) eliminates hydrolysis of protein peptide bonds of the external hyperplastic tissue, which is fulfilled by a complex of ingredients including said nitric acid of said caustic portion, said acetic acid of said caustic portion, said pyruvic acid of said caustic portion, said maleic acid of said caustic portion, and said l-histidine of said caustic portion.

23. The topical composition of claim 5, wherein said white activated charcoal powder of said detoxifying and cleansing portion and said l-histidine of said caustic portion provides timely regeneration of healthy skin tissue after the external hyperplastic tissue has been treated with said topical composition.

24. The topical composition of claim 5, wherein said delivery system of said b-cyclodextrine of said caustic portion prevents damage to surrounding healthy skin tissue.

25. The topical composition of claim 5, wherein said metallic copper of said caustic portion neutralizes destruction potential.

26. The topical composition of claim 1, wherein said white activated charcoal powder of said detoxifying and cleansing portion eliminates undesirable maceration, inflammatory, or coarse keratolytic process that can lead to spread of the virus to other skin areas.

27. The topical composition of claim 5, wherein said l-histidine of said caustic portion and said white activated charcoal powder of said detoxifying and cleansing portion eliminates pain during and after use.

* * * * *